(12) United States Patent
Morgan (10) Patent No.: US 7,212,871 B1
(45) Date of Patent: May 1, 2007

(54) EPICARDIAL AND MYOCARDIAL LEADS FOR IMPLANTING IN THE HEART BY THORACOTOMY OR PORT ACCESS SURGERIES WITH DETACHABLE ELECTRODE TIP

(75) Inventor: Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 177 days.

(21) Appl. No.: 10/745,839

(22) Filed: Dec. 24, 2003

(51) Int. Cl.
  *A61N 1/05* (2006.01)
(52) U.S. Cl. .................................................. 607/129
(58) Field of Classification Search ......... 607/129–131
  See application file for complete search history.

(56) References Cited

U.S. PATENT DOCUMENTS

| | | | | |
|---|---|---|---|---|
| 3,880,169 | A | * | 4/1975 | Starr et al. ................... 607/129 |
| 4,125,116 | A | * | 11/1978 | Fischell ....................... 607/129 |
| 4,291,707 | A | * | 9/1981 | Heilman et al. ............. 128/784 |
| 4,607,644 | A | * | 8/1986 | Pohndorf ..................... 450/61 |
| 4,972,833 | A | | 11/1990 | Wildon .................... 128/419 P |
| 5,176,135 | A | | 1/1993 | Fain et al. ............... 128/419 D |
| 5,336,252 | A | | 8/1994 | Cohen ......................... 607/119 |
| 5,545,207 | A | * | 8/1996 | Smits et al. ................. 607/130 |
| 5,846,196 | A | * | 12/1998 | Siekmeyer et al. ........... 600/374 |
| 5,871,532 | A | | 2/1999 | Schroeppel .................. 607/128 |
| 6,408,213 | B1 | * | 6/2002 | Bartig et al. ................ 607/122 |
| 6,459,937 | B1 | | 10/2002 | Morgan et al. ............. 607/126 |
| 6,501,993 | B2 | | 12/2002 | Morgan et al. ............. 607/122 |
| 2002/0103522 | A1 | * | 8/2002 | Swoyer et al. ............... 607/116 |
| 2002/0143379 | A1 | * | 10/2002 | Morgan et al. ............. 607/122 |
| 2003/0074041 | A1 | | 4/2003 | Parry et al. ................. 607/130 |
| 2004/0176830 | A1 | * | 9/2004 | Fang .......................... 607/129 |
| 2004/0215301 | A1 | * | 10/2004 | Lokhoff et al. ............. 607/116 |

\* cited by examiner

*Primary Examiner*—Scott M. Getzow (57) ABSTRACT

A medical electrical lead to conduct electrical stimulation and/or signals between an electrical stimulator and a heart site includes an elongated lead body extending to a proximal connector for attachment to the electrical stimulator. An electrode head at the distal end includes an electrode tip member for fixation to the heart and an electrode backing member fixed to the lead body is releasably attachable to the electrode tip member for transmission of electrical signals between the heart and the electrical stimulator. The electrode tip member may include a first non-conductive base with an outwardly projecting tip electrode and a first mounting member projecting oppositely away from the non-conductive base. The electrode backing member includes a second non-conductive base and a second mounting member thereon adapted for mounting engagement with the first mounting member for selectively releasably but firmly integrating the electrode tip member and the electrode backing member.

16 Claims, 11 Drawing Sheets

EPICARDIAL AND MYOCARDIAL LEADS FOR IMPLANTING IN THE HEART BY THORACOTOMY OR PORT ACCESS SURGERIES WITH DETACHABLE ELECTRODE TIP

FIELD OF THE INVENTION

The present invention relates generally to implantable medical devices for providing stimulating pulses to selected body tissue, and more particularly, to implantable cardiac stimulation leads of the epicardial type.

BACKGROUND OF THE INVENTION

Prior to the advent of endocardially implanted leads and associated surgical implantation techniques, surgeons and cardiologists traditionally relied on epicardial leads for cardiac stimulation and diagnosis. Median sternotomy or anterior thoracotomy were commonly used techniques to access the pericardium for epicardial lead implantation. Both techniques involve a significant incision and the post-operative issues associated with large incisions, such as recuperation time, pain, risk of infection, and cosmetic results.

Patients and practitioners alike favor the use of endocardial leads for cardiac stimulation in most circumstances. The benefits of transvenous implantation are many, including improved post-operative cosmetic appearance, faster wound healing, less post-operative pain, and improved flexibility in electrode placement. In addition, many areas of the myocardium that do not normally lend themselves to epicardial stimulation, such as the interventricular septum or the coronary sinus, may be readily paced endocardially.

Despite the advantages associated with endocardial implantation, epicardial cardiac stimulation is still medically indicated for many patients, particularly children. Although the various indications for epicardial lead fixation in pediatric patients are numerous, some common factors include small stature, congenital heart defects with residual or potential right to left shunting, or lack of venous access to the chamber requiring pacing.

Early designs for myocardial leads required relatively large screw-in electrodes that were intended for ventricular applications only. Follow-on prior art electrode designs utilized a stab-on electrode that was configured to be inserted into the atrial or the ventricular myocardium in a direction almost tangential to, and just under, the epicardial surface. After the stab-on step, the electrode body was then sutured to the epicardial surface for stabilization. These prior art electrodes were most commonly implanted via median sternotomy or anterior thoracotomy The advent of thoracoscopy in cardiac surgery has shown promise as a technique to enable surgeons to implant epicardial leads without sternotomy or thoracotomy. Thoracoscopy normally involves penetration of the chest cavity with two or more tubular introducers that are passed through small incisions in the chest wall. Illumination devices, cutting instruments, sutures, and the like may be inserted into the chest cavity via the introducers.

Despite the promise of thoracoscopy, many conventional epicardial leads utilize a widened suture pad that is normally disk-shaped and includes one or more suture holes for guiding a suture needle into the epicardium. These disk-like suture pads may present the surgeon with certain difficulties during insertion via a typical thoracoscopy introducer. To begin with, there is the potential for the suture pad to resist movement through the introducer. Unless extreme caution is exercised, the lead may be damaged. To avoid the potential for snagging the lead, surgeons may have to use a larger than necessary introducer, resulting in a larger incision, more scarring, and potentially more post-operative pain for the patient. In addition, if a conventional suture pad epicardial lead must be relocated due to improper threshold or some other indication, the surgeon must expend time and effort cutting the existing sutures and sewing the pad to the new location.

Another solution proposed for myocardial lead implantation utilizes a sutureless screw-in electrode. The electrode is screwed into the myocardium perpendicular to the surface of the epicardium while the lead is laid approximately parallel to the epicardium surface. The arrangement produces an almost 90 degree bend in the lead just proximal to the electrode that may give rise to forces capable of dislodging the electrode and/or injuring the epicardium, particularly in view of the normally vigorous cyclic movement of the epicardium. Injury to the epicardium may also occur if the rib cage is compressed against the 90 degree bend during rough play or other exercise.

Another existing lead design incorporates a projectable side hook that is normally biased in a retracted position by a coil spring. The side hook is moved to an extended position by application of axial force from a stylet to an internally disposed leg of the side hook that includes a roller disposed in an arcuate channel. The fabrication of this system requires a series of complex molding and machining steps, often under relatively tight tolerances. In operation, this system relies on a series of cooperating rollers, curved slots, and springs that may be subject to malfunction during implantation, and requires the surgeon to simultaneously apply axial force on a stylet and torsional force on the lead.

Typical of the patented prior art is U.S. Pat. No. 4,972,833 to Wildon which discloses a pacing lead assembly with an epicardial lead placed via needle access through the chest wall intended to be temporarily implanted in the body of a cardiac patient before the pericardium and chest wall are closed. Another instance is U.S. Pat. No. 5,176,135 to Fain et al. which discloses an implantable lead system that includes an epicardial lead placed through the abdomen or thorax and employs various configurations of electrodes when in the deployed state. U.S. Pat. No. 5,336,252 discloses a system for implanting electric leads in the pericardial space of a heart with an electrical lead being advanced, through a channel earlier positioned in an access hole through the pericardium, to penetrate the pericardial space and is secured with an anchor flange at the end of the electrical lead. U.S. Pat. No. 5,871,532 to Schroeppel discloses a lead assembly for fixation to a human heart via thoracoscopy. The lead assembly includes a tubular introducer that is passed through the chest wall of a patient and used to place the lead with a detachable epicardial electrode proximate the epicardium. As a final example of known lead constructions, U.S. Patent Application Publication No. US 2003/0074041 to Parry et al. discloses an epicardial electrode preferably implanted by performing a thoracoscopy of the thorax of the patient to visualize the site of the epicardium through a thoracoscope and to provide a pathway to the site of the epicardium.

SUMMARY

A medical electrical lead to conduct electrical stimulation and/or signals between an electrical stimulator and a heart site includes an elongated lead body extending to a proximal connector for attachment to the electrical stimulator. An electrode head at the distal end includes an electrode tip member for fixation to the heart and an electrode backing member fixed to the lead body is releasably attachable to the electrode tip member for transmission of electrical signals between the heart and the electrical stimulator. The electrode tip member may include a first base with an outwardly projecting tip electrode and a first mounting member projecting oppositely away from the base. The electrode backing member includes a second base and a second mounting member thereon adapted for mounting engagement with the first mounting member for selectively releasably but firmly integrating the electrode tip member and the electrode backing member.

Generally, when the need for permanent or temporary pacing of the heart is realized in cardiac surgery procedure, an epicardial or myocardial pacing lead is routinely used. Attaching leads to the heart's epicardial surface is a straight forward process. Myocardial or epicardial lead placement is performed when satisfactory placement of a transvenous lead is not possible due to compromised venous system, a prosthetic tricuspid valve, heart chamber dilation (CHF), or is placed in a very small child or infant.

Replacement of a chronically implanted myocardial lead is necessary when there is a fracture in the lead body or electrode, infection, or the electrode site reaches a high enough threshold level to achieve exit block. Replacing the lead on the heart's surface is a very tedious process that requires a highly skilled surgical team and longer stays in the hospital for the patient. The risk of internal bleeding within the thoracic cavity is high when attempting to remove the lead from the heart's surface and the thoracic cavity.

Thus, what is described herein is an epicardial or myocardial lead that features a detachable tip electrode. The electrode can be either a unipolar or bipolar design configuration and can be fixated to the heart by a helical screw or tied down with suture material. The lead is handled during implant surgery as a standard epicardial or myocardial lead and implanted using standard procedures.

To prevent or minimize trauma to heart, the lead is detachable at the lead body/electrode interface. The lead body is then removed in its entirety leaving the distal tip with the electrode remaining on the heart's surface. A new lead body would then be snapped into place on the existing implanted electrode and tunneled up though the chest to be connected to a pacemaker. This procedure would be done only if the lead body has failed in someway and must be replaced. The electrode remains untouched.

Another feature of the lead is if the electrode achieves exit block and the pacemaker is no longer able to deliver a high enough electrical energy to pace the heart or if the electrode has failed for other reasons, the lead body may be detached from the electrode tip. The lead body can be either removed completely or reattach anew. The implant site with the encapsulated electrode tip is abandoned. A new implant site is located and a new lead is implanted. In this way, the heart has minimally traumatized and complications such as internal bleeding are greatly reduced.

Still another feature of the lead is that it can be accessed by port access surgery (keyhole). Detaching the electrode and implanting a new lead or new lead body can be done all through the port access system with tools designed for this system. This procedure is a minimally invasive surgery that reduces the injury and trauma that is typical in the open chest surgery. This can help reduce the time spent in surgery and patient recovery.

BRIEF DESCRIPTION OF THE DRAWINGS

The foregoing aspects and other features are explained in the following description, taken in connection with the accompanying drawings, wherein.

DETAILED DESCRIPTION OF THE PREFERRED EMBODIMENT

Figure 1:
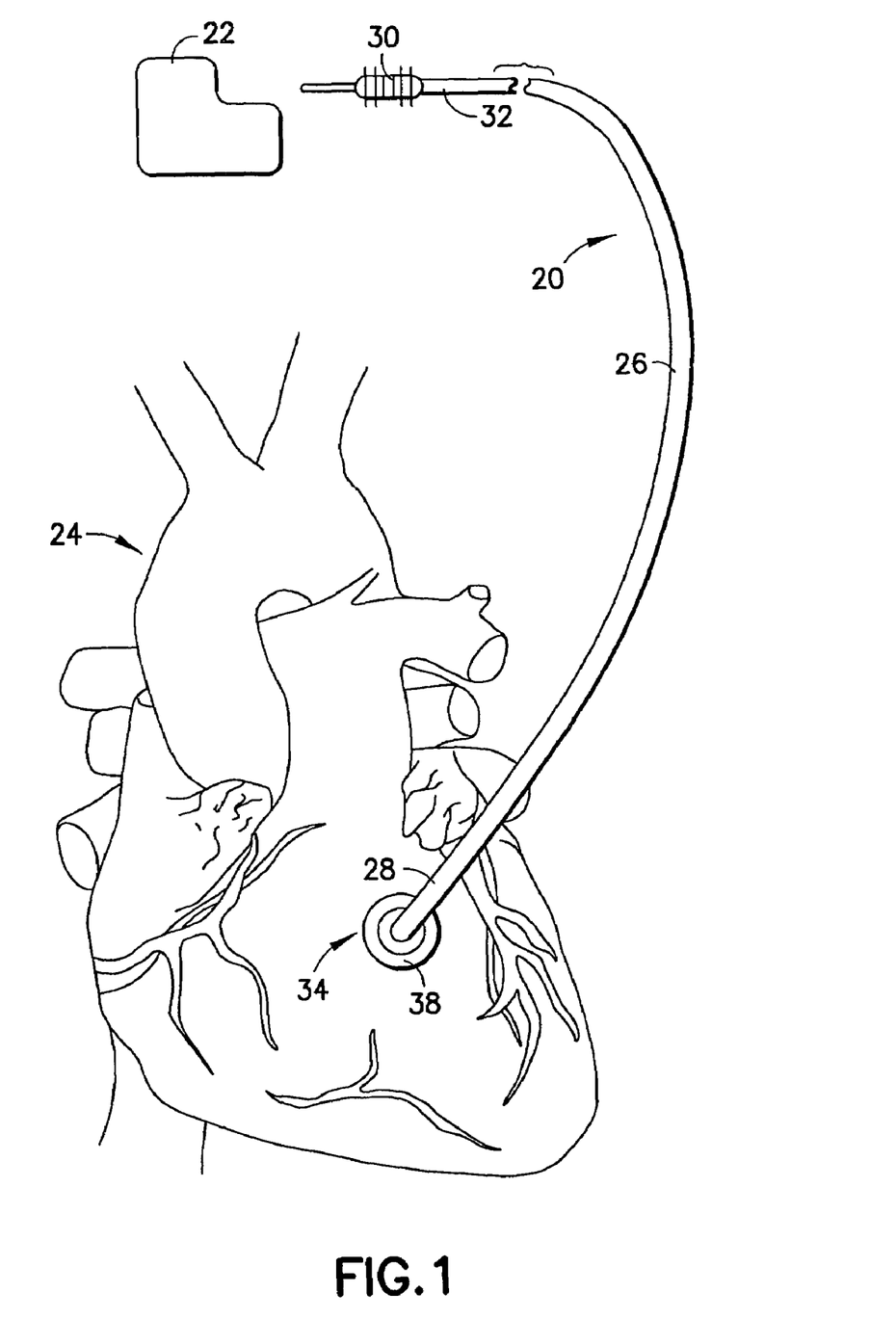
FIG. 1 is a diagrammatic perspective view illustrating an implanted lead system for providing electrical stimulation of a heart employing an implanted lead according to one illustrative embodiment.
Figures 2, 3:
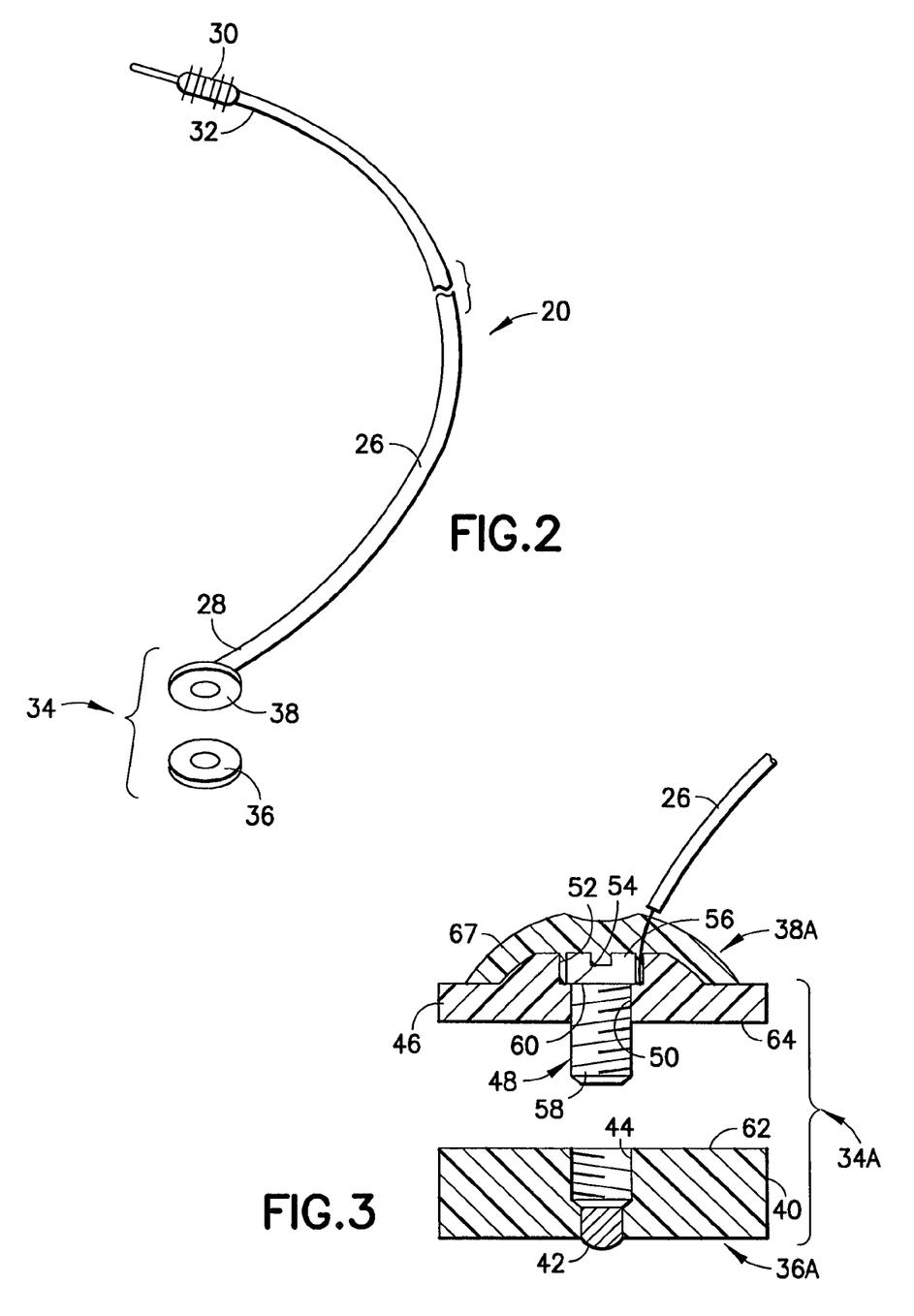
FIG. 2 is an exploded perspective view of a lead illustrated in FIG. 1 in a detached condition.
FIG. 3 is a detail elevation view, in cross section, of one embodiment of an electrode head with an electrode tip member and an electrode backing member in their separated condition.

Refer now to the drawings and, initially, to FIGS. 1 and 2 in which are shown diagrammatic perspective views of a medical electrical, epicardial or myocardial lead 20 for use in association with an electrical stimulator 22 such as a pacemaker or defibrillator providing electrical stimulation to a heart 24. Although the lead 20 will be described with reference to the embodiments shown in the drawings, it should be understood that lead 20 can be embodied in many alternate forms or embodiments. In addition, any suitable size, shape or type of elements or materials could be used.

The lead 20 is adapted to conduct electrical stimulation from the electrical stimulator 22, which may be, alternatively and selectively, implantable or external to a site of the heart 24 and to conduct electrical signals of the heart from the site to the stimulator. The lead 20 includes an elongated lead body 26 extending from a lead body distal end 28 to a connector 30 at the lead body proximal end 32 for mechanical and electrical attachment to the electrical stimulator 22. An electrode head 34 is provided at the lead body distal end 28 and includes an electrode tip member 36 (FIG. 2) adapted to be fixated to the heart and an electrode backing member 38 fixed to the distal end 28 of the lead body 26 and releasably attachable to the electrode tip member. When the electrode tip member 36 and the electrode backing member 38 are attached, electrical signals can be transmitted between the heart 24 and the electrical stimulator 22.

Turn now to FIG. 3 for the description of one embodiment of the lead assembly. In this instance, an electrode head 34A includes an electrode tip member 36A with a first non-conductive base 40 of polyurethane or other suitable material and a tip electrode 42 mounted on and projecting away from the non-conductive base in one direction. The non-conductive base 40 has a first mounting member in the form of a centrally located tapped bore 44 which is directed away from the tip electrode 42. An electrode backing member 38A includes a second non-conductive base 46 also composed of polyurethane or other suitable material and a second mounting member in the form of a screw member 48 is cooperatively received on the second non-conductive base and adapted for mounting engagement with the first mounting member, specifically, the tapped bore 44 for releasably but firmly integrating the electrode tip member 36A and the electrode backing member 38A as a unit (see FIG. 3A).

Figures 3A, 4, 5:
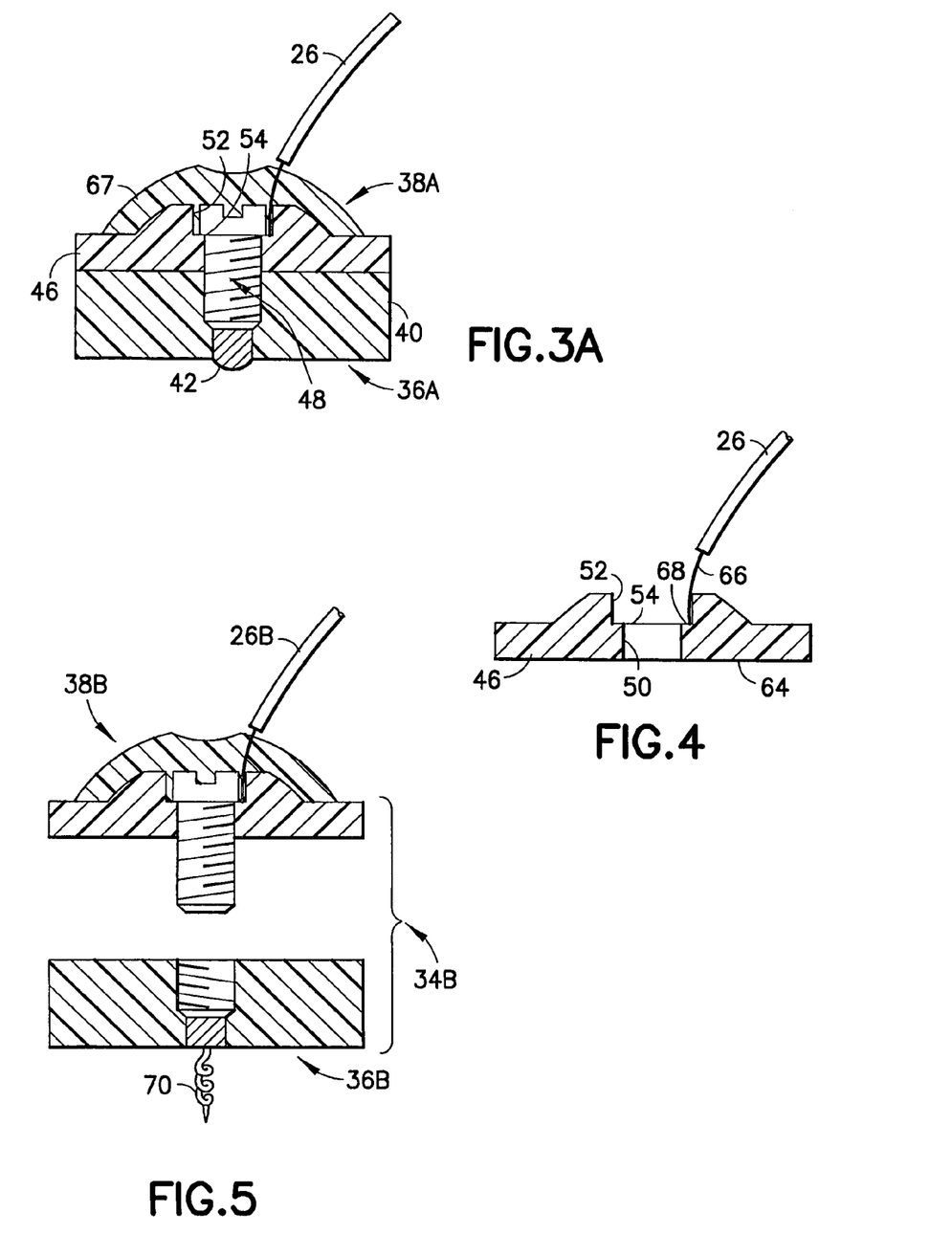
FIG. 3A is a detail elevation view, in cross section, of the embodiment of the electrode head illustrated in FIG. 3 in its engaged condition.
FIG. 4 is a detail elevation view, in cross section, of a part of the electrode head illustrated in FIG. 3.
FIG. 5 is a detail elevation view, in cross section, of another embodiment of an electrode head with an electrode tip member and an electrode backing member in their separated condition.

Viewing FIGS. 3 and 4, the second non-conductive base 46 has a central smooth bore 50 nearest the electrode tip member 36, an enlarged counterbore 52 in communication with the central bore 50 and extending farther away from the electrode tip member, and an annular shelf 54 intermediate the central bore and the enlarged counterbore. The screw member 48 (FIG. 3) includes a head 56, a threaded shank 58, and a shoulder 60 intermediate the head and the threaded shank. The threaded shank 58 is slidably received through the central bore 50 with the shoulder 60 of the screw member 48 engageably received on the annular shelf 54. The threaded shank 58 is threadedly engageable with the tapped bore 44 of the base 40 and rotated about its longitudinal axis until firm integration of the electrode tip member 36A and of the electrode backing member 38A has occurred as seen in FIG. 3A.

As clearly seen in FIGS. 3 and 4, the first non-conductive base 40 has a first planar surface 62 facing the second non-conductive base 46 and the second non-conductive base 46 has a second planar surface 64 facing the first planar surface. The first and second planar surfaces 62, 64, respectively, are contiguously engaged when the electrode tip member 36A and the electrode backing member 38A are firmly integrated as a unit (FIG. 3A).

To assure the integrity and biocompatibility of the electrode head 34A as well as to constrain the electrical path between a conductor 66 of the lead body 26 (FIG. 4) and the tip electrode 42, a non-conductive cap member 67 of polyurethane or other suitable composition (FIG. 3) is applied to the base 46 to proximally overlie the electrode backing member 38. Further, in regard to the electrical path, a portion of the annular shelf 54 may be metallized as indicated at 68 (FIG. 4) to assure electrical continuity between the conductor 66, the screw member 48 when its head 56 is engaged with the metallized surface 68 of the annular shelf 54, and the tip electrode 42.

In the instance of the FIGS. 3, 3A, and 4 embodiment, the tip electrode 42 is a passive fixation electrode, typically being held in place by use of suture material.

In another instance illustrated in FIG. 5, an electrode head 34B is modified such that a tip electrode 36B is an active fixation electrode utilizing a helical screw 70 in the usual fashion. For the electrode head 34B, an electrode backing member 38B remains unchanged from the FIGS. 3, 3A, and 4 embodiment.

Figure 6:
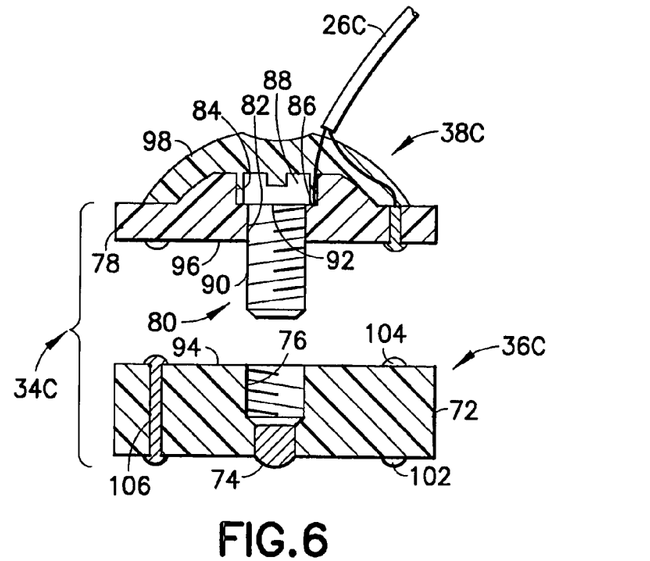
FIG. 6 is a detail elevation view, in cross section, of still another embodiment of an electrode head with an electrode tip member and an electrode backing member in their separated condition.

For another embodiment of the lead assembly, turn now to FIG. 6 which illustrates an electrode head 34C modified to include an electrode tip member 36C with a first non-conductive base 72 of polyurethane or other suitable material and a tip electrode 74 mounted on and projecting away from the non-conductive base in one direction. The non-conductive base 72 has a first mounting member in the form of a centrally located tapped bore 76 which is directed away from the tip electrode 74. An electrode backing member 38C includes a second non-conductive base 78 also composed of polyurethane or other suitable material and a second mounting member in the form of a screw member 80 is cooperatively received on the second non-conductive base and adapted for mounting engagement with the first mounting member, specifically, the tapped bore 76 for releasably but firmly integrating the electrode tip member 36C and the electrode backing member 38C as a unit (see FIG. 6A).

Figure 6A:
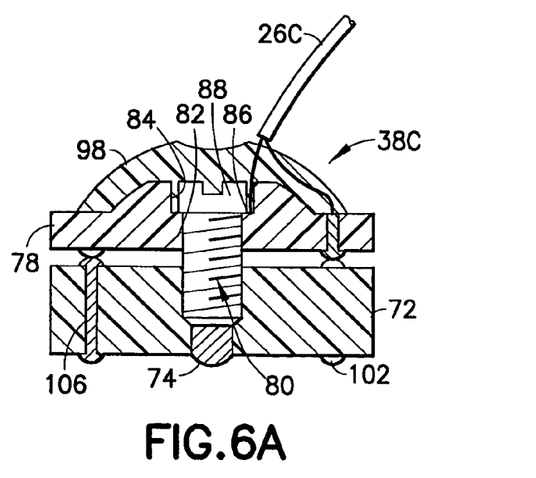
FIG. 6A is a detail elevation view, in cross section, of the embodiment of the electrode head illustrated in FIG. 6 in its engaged condition.
Figure 7:
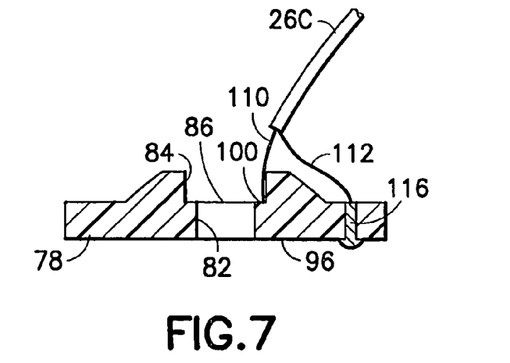
FIG. 7 is a detail elevation view, in cross section, of a part of the electrode head illustrated in FIG. 6.

Viewing FIGS. 6 and 7, the second non-conductive base 78 has a central smooth bore 82 nearest the electrode tip member 36C, an enlarged counterbore 84 in communication with the central bore 82 and extending farther away from the electrode tip member, and an annular shelf 86 intermediate the central bore and the enlarged counterbore. The screw member 80 includes a head 88, a threaded shank 90, and a shoulder 92 intermediate the head and the threaded shank. The threaded shank 90 is slidably received through the central bore 82 with the shoulder 92 of the screw member 80 engageably received on the annular shelf 86. The threaded shank 90 is threadedly engaged with the tapped bore 76 of the base 72 and rotated about its axis until firm integration of the electrode tip member 36C and of the electrode backing member 38C has occurred as seen in FIG. 6A.

As clearly seen in FIGS. 6 and 7, the first non-conductive base 72 has a first planar surface 94 facing the second non-conductive base 78 and the second non-conductive base 78 has a second planar surface 96 facing the first planar surface. The first and second planar surfaces 94, 96, respectively, are contiguously engaged when the electrode tip member 36C and the electrode backing member 38C are firmly integrated as a unit (see FIG. 6A).

As in the earlier described embodiment, to assure the integrity and biocompatibility of the electrode head 34C as well as to constrain the electrical path between the conductor 110 of the lead body 26C (FIG. 7) and the tip electrode 74, a non-conductive cap member 98 of polyurethane or other suitable composition is applied to the base 78 to proximally overlie the electrode backing member 38C. Further, in regard to the electrical path, a portion of the annular shelf 86 may be metallized as indicated at 100 (FIG. 7) to assure electrical continuity between the conductor 110, the screw member 80 when its head 88 is engaged with the metallized surface 100 of the annular shelf 86, and the tip electrode 74.

Figure 8:
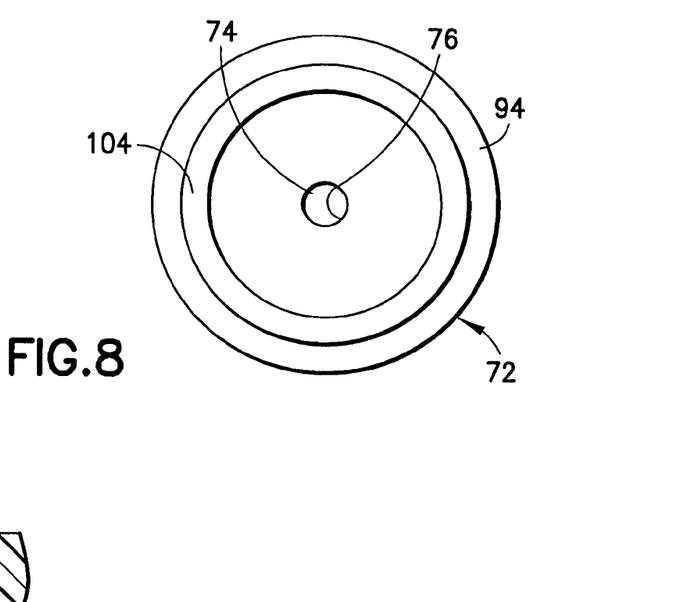
FIG. 8 is a top plan view of components illustrated in FIG. 6.
Figure 9:
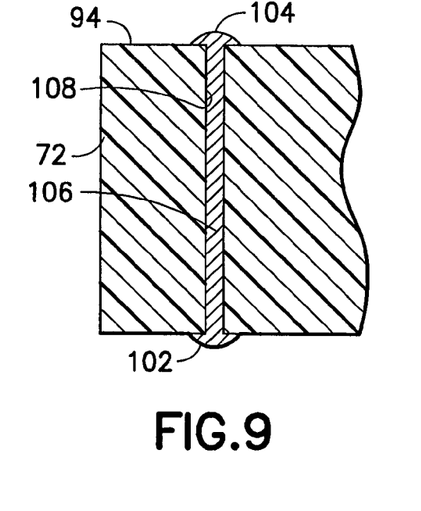
FIG. 9 is a detail cross section view of components illustrated in FIG. 6.
Figure 10:
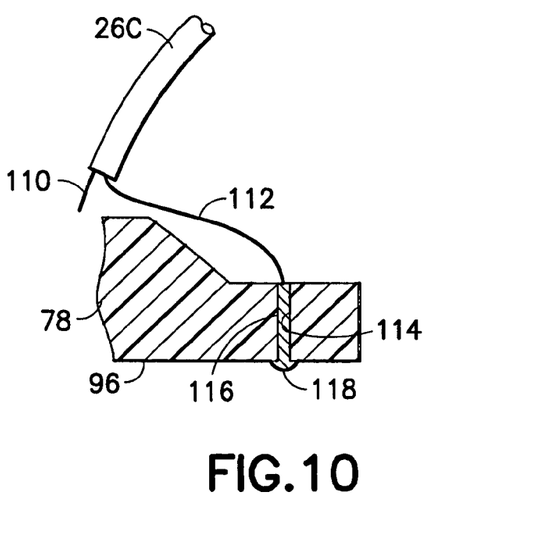
FIG. 10 is another detail cross section view of components illustrated in FIG. 6.

Continuing with the description of the FIGS. 6, 6A, and 7 embodiment, and with further reference to FIGS. 8, 9, and 10, a ring electrode 102 is mounted on and projects away from the first non-conductive base 72 in one direction, the ring electrode being spaced from the tip electrode 74. A ring contact 104 (see especially FIG. 8) is mounted on the first planar surface 94 and a connection branch 106 is received in a bore 108 through the first non-conductive base 72 electrically connecting the ring electrode 102 and the ring contact 104. In this instance, a lead body 26C includes a first lead 110 attached to the metallized surface 100 for connection, via the screw member 80, with the tip electrode 74. The lead body 26C also includes a second lead 112 attached through a bore 114 containing a connection branch 116 in the second non-conductive base 78 to a contact 118 on the second planar surface 96 for connection with the ring contact 104 when the electrode tip member 36C and the electrode backing member 38C are firmly integrated as a unit.

In the instance of the FIGS. 6–10 embodiment, the tip electrode 74 is a passive fixation electrode, typically being held in place by use of suture material.

Figures 11, 12, 12A:
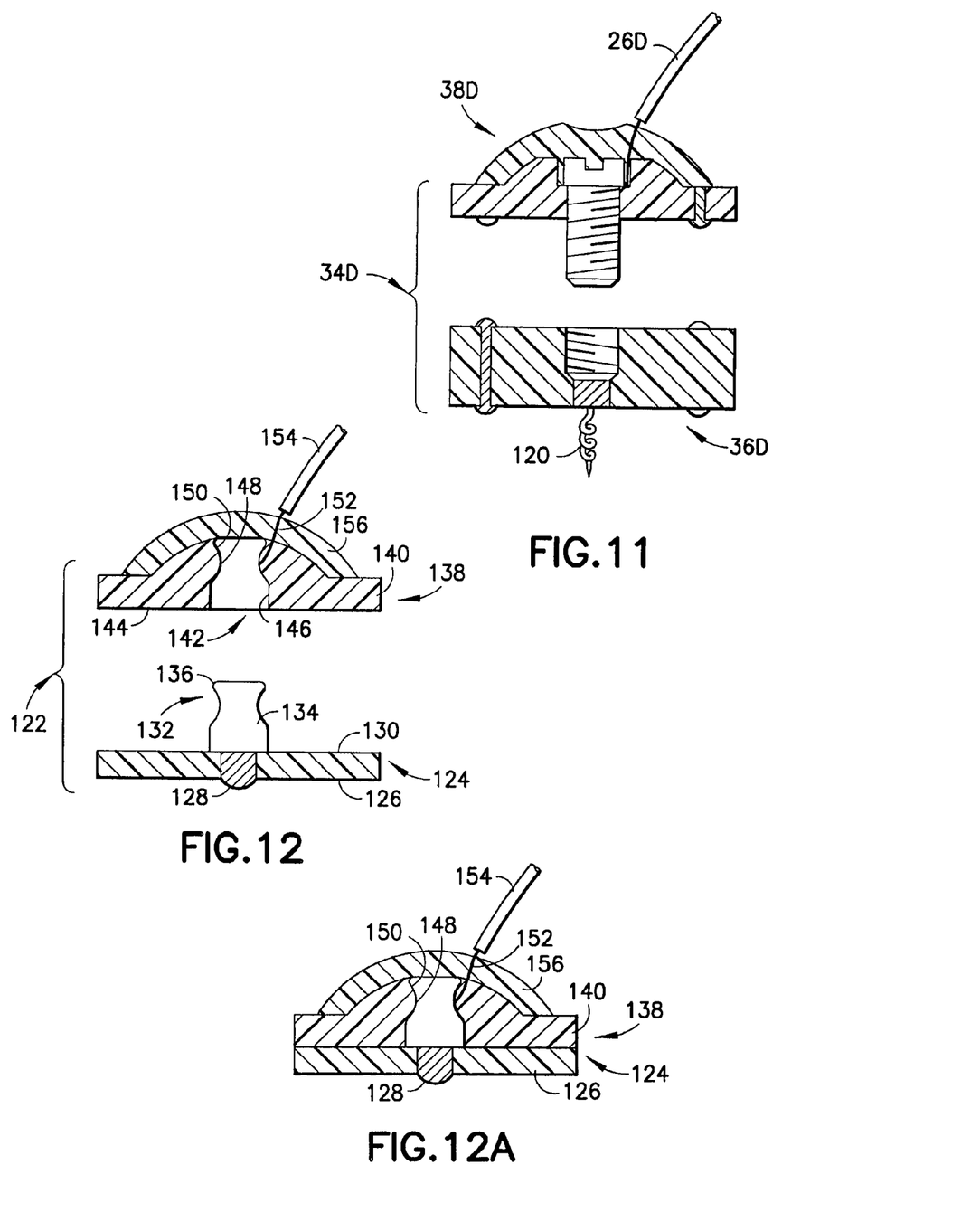
FIG. 11 is a detail elevation view, in cross section, of yet another embodiment of an electrode head with an electrode tip member and an electrode backing member in their separated condition.
FIG. 12 is a detail elevation view, in cross section, of still another embodiment of an electrode head with an electrode tip member and an electrode backing member in their separated condition.
FIG. 12A is a detail elevation view, in cross section, of the embodiment of the electrode head illustrated in FIG. 12 in its engaged condition.

In yet another instance illustrated in FIG. 11, an electrode head 34D is modified such that a tip electrode 36D is an active fixation electrode utilizing a helical screw 120 in the usual fashion. For the electrode head 34D, an electrode backing member 38D remains unchanged from the FIG. 6 embodiment.

Turn now to FIG. 12 for another embodiment of the lead assembly. In this instance, an electrode head 122 includes an electrode tip member 124 with a first non-conductive base 126 of polyurethane or other suitable material and a tip electrode 128 mounted on and projecting away from the non-conductive base in one direction. The first non-conductive base 126 has a first planar surface 130 and a first mounting member 132 directed away from the tip electrode 128 includes a post 134 having a contoured peripheral outer surface upstanding from the first planar surface 130 and extending to an outwardly projecting annular rim 136.

An electrode backing member 138 includes a second non-conductive base 140 and a second mounting member 142 is cooperatively received on the second non-conductive base and adapted for mounting engagement with the post 134 for releasably but firmly integrating the electrode tip member 124 and the electrode backing member 138 as a unit (see FIG. 12A). The second non-conductive base 140 has a second planar surface 144 and, defining the second mounting member 142, the base 140 has a contoured central bore 146 extending away from the second planar surface and generally configured congruently to the upstanding post 134, having an intermediate annular ridge 148 and terminating beyond the annular ridge at an annular valley region 150 distant from the second planar surface. With this construction, the upstanding post 134 may be slidably but fittingly received through the central bore 146 until the annular rim 136 engages the annular ridge 148, momentarily enlarging the diameter of the annular ridge, then is contiguously received by the annular valley region 150 and, simultaneously, the first and second planar surfaces 130, 144, respectively, become contiguously engaged whereupon firm integration of the electrode tip member 124 and of the electrode backing member 138 occurs (see FIG. 12A).

Figure 13:
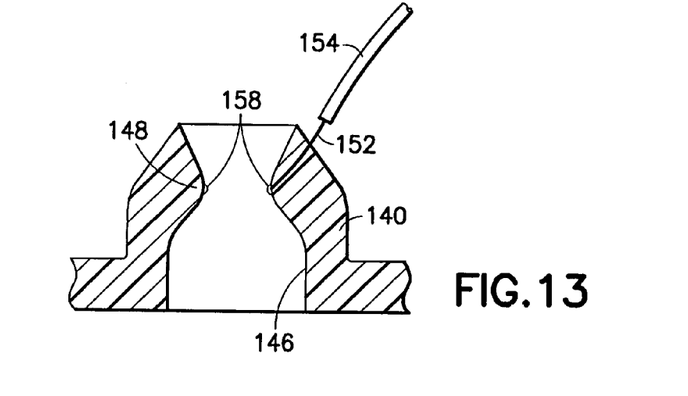
FIG. 13 is a detail elevation view, in cross section, of a part of the electrode head illustrated in FIG. 12.

As in the previously described embodiments, to assure the integrity and biocompatibility of the electrode head 122 as well as to constrain the electrical path between a conductor 152 of a lead body 154 (FIGS. 12 and 13) and the tip electrode 128, a non-conductive cap member 156 of polyurethane or other suitable composition is applied to the base 140 to proximally overlie the electrode backing member 138. Further, in regard to the electrical path, a portion of the annular ridge 148 may be metallized as indicated at 158 (FIG. 13) to assure electrical continuity between the conductor 152, the post 134 when it is fully received in the central bore 146, and the tip electrode 128.

In the instance of the FIG. 12 embodiment, the tip electrode 128 is a passive fixation electrode, typically being held in place by use of suture material.

Figures 14, 15:
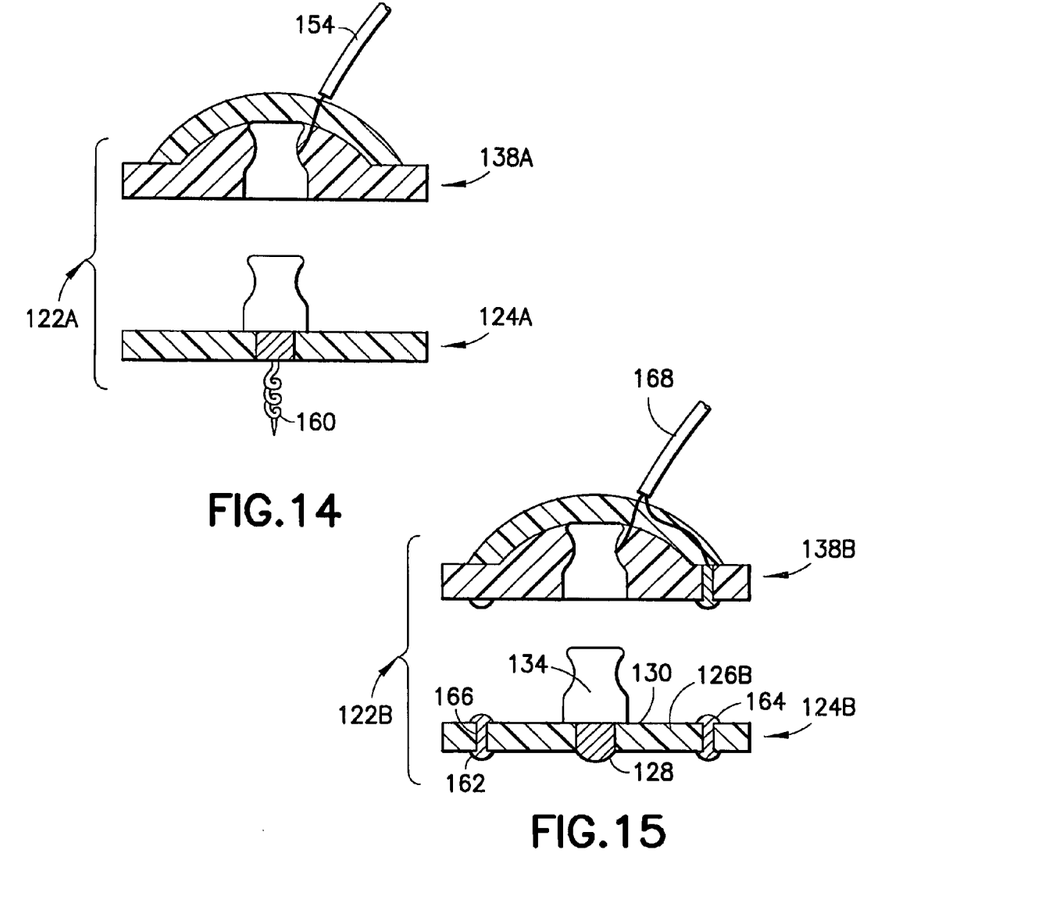
FIG. 14 is a detail elevation view, in cross section, of still another embodiment of an electrode head with an electrode tip member and an electrode backing member in their separated condition.
FIG. 15 is a detail elevation view, in cross section, of yet another embodiment of an electrode head with an electrode tip member and an electrode backing member in their separated condition.

In another instance illustrated in FIG. 14, an electrode head 122A is modified such that a tip electrode 124A is an active fixation electrode utilizing a helical screw 160 in the usual fashion. For the electrode head 122A, an electrode backing member 138A remains unchanged from the FIG. 12 embodiment. As in previous embodiments, the electrode heads 122 and 122A (FIGS. 12 and 14, respectively) employ a unipolar tip electrode.

Figure 16:
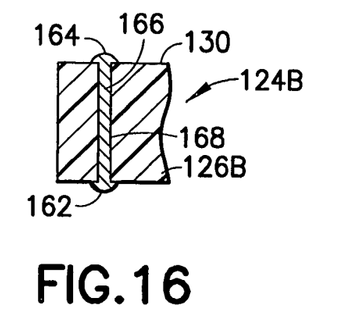
FIG. 16 is a detail cross section view of components illustrated in FIG. 15.
Figure 17:
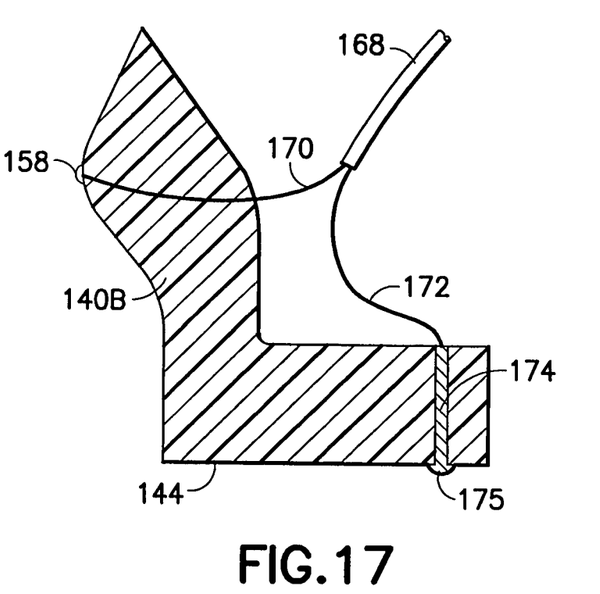
FIG. 17 is another detail cross section view of components illustrated in FIG. 15.

Turn now to FIGS. 15, 16, and 17 which present a generally similar construction but one of a bipolar electrode configuration. In this instance, a ring electrode 162 is mounted on and projects away from the first non-conductive base 126B in one direction, the ring electrode being spaced from the tip electrode 128. A ring contact 164 is mounted on the first planar surface 130 and a connection branch 166 (FIG. 16) received in a bore 168 through the first non-conductive base 126B electrically connects the ring electrode 162 and the ring contact.

Viewing especially FIG. 17, a lead body 168 includes a first lead 170 attached to the annular metallized surface of a second non-conductive base 140B for connection, via post 134 with the tip electrode 128 and a second lead 172 attached via a connection branch 174 in a bore in the second non-conductive base 140B to a second contact 175 on the second planar surface 144 for connection with the ring electrode 162 when the electrode tip member 124B and the electrode backing member 138B are firmly integrated as a unit.

Figure 18:
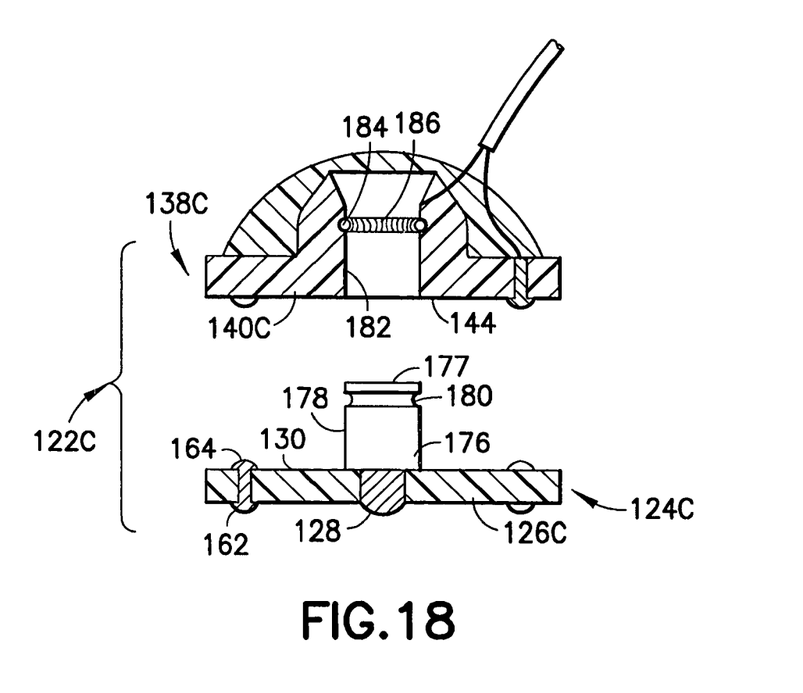
FIG. 18 is a detail elevation view, in cross section, of yet a further embodiment of an electrode head with an electrode tip member and an electrode backing member in their separated condition.

A modification of the FIG. 15 embodiment, which may also be applied to the FIG. 12 (unipolar) configuration, is provided in FIG. 18. In this instance, a modified post 176 has an extreme end 177 and an outer peripheral surface 178 with a first annular groove 180 positioned intermediate the extreme end 177 and the first planar surface 130 of a first non-conductive base 126C. The second non-conductive base 140C has a second planar surface 144 and a central bore 182 extending away from the second planar surface and a second annular groove 184 spaced from the second planar surface. An annular, or donut shaped, coil spring 186 is fittingly received in the annular groove 184 such that the upstanding post 176 may be slidably received through the central bore 182 until the extreme end 177 engages the coil spring. With continued movement of the post 176 relative to the coil spring 186, the first annular groove 180 receivably engages the annular coil spring and, simultaneously, the first and second planar surfaces become contiguously engaged whereupon firm integration of the electrode tip member 124C and of the electrode backing member 138C occurs. In all other respects, the electrode head 122C is similar to the electrode head 122B.

In the instance of the FIGS. 15 and 18 embodiments, the tip electrode 128 is a passive fixation electrode, typically being held in place by use of suture material.

Figures 19, 20, 20A, 20B:
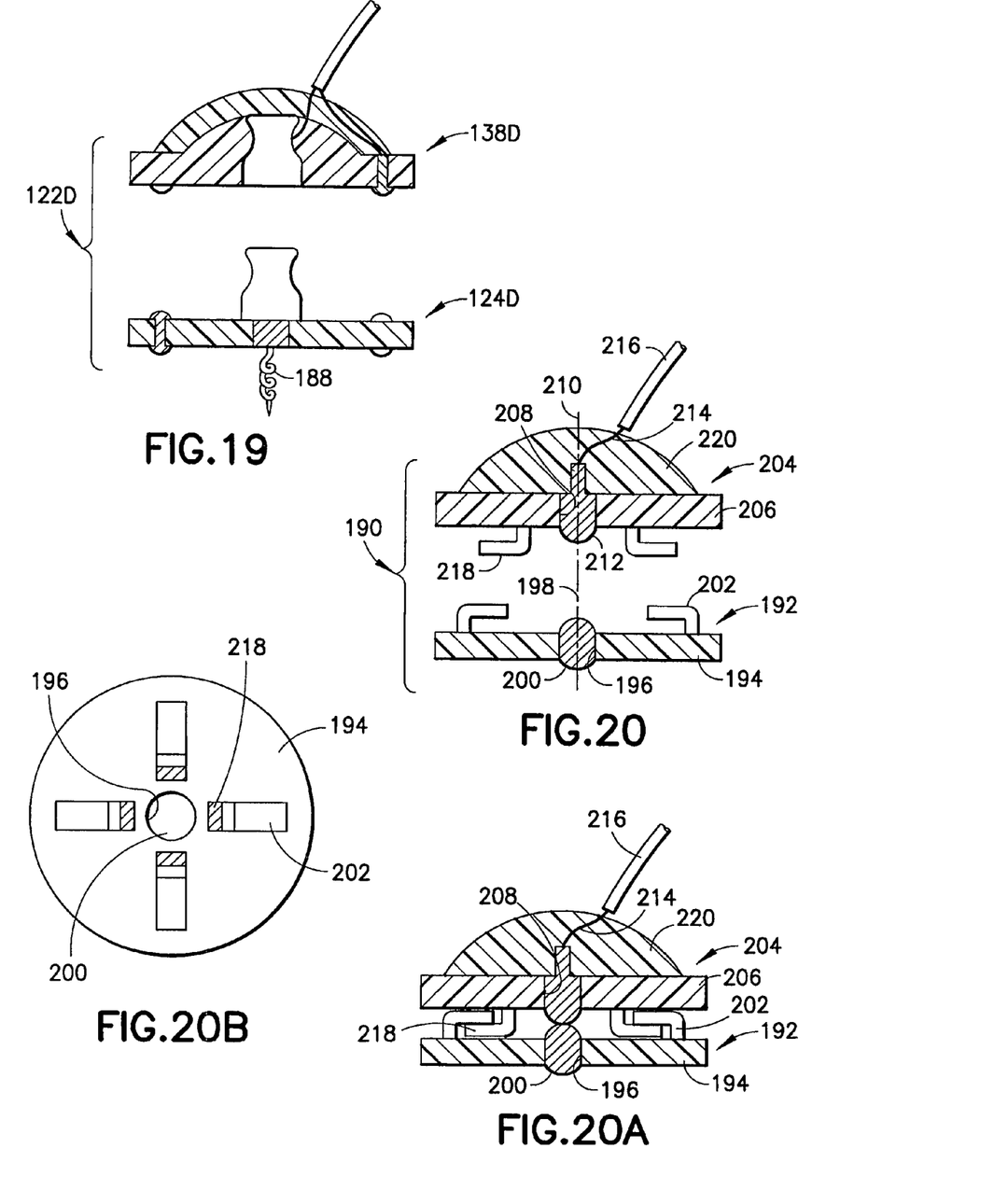
FIG. 19 is a detail elevation view, in cross section, of still a further embodiment of an electrode head with an electrode tip member and an electrode backing member in their separated condition.
FIG. 20 is a detail elevation view, in cross section, of yet another embodiment of an electrode head with an electrode tip member and an electrode backing member in their separated condition.
FIG. 20A is a detail elevation view, in cross section, of the embodiment of the electrode head illustrated in FIG. 20 in its engaged condition.
FIG. 20B is a cross section view taken generally along line 20B—20B in FIG. 20A.

In yet another instance illustrated in FIG. 19, an electrode head 122D is modified such that a tip electrode 124D is an active fixation electrode utilizing a helical screw 188 in the usual fashion. For the electrode head 122D, an electrode backing member 138D remains unchanged from the FIG. 15 embodiment.

Figures 21, 22:
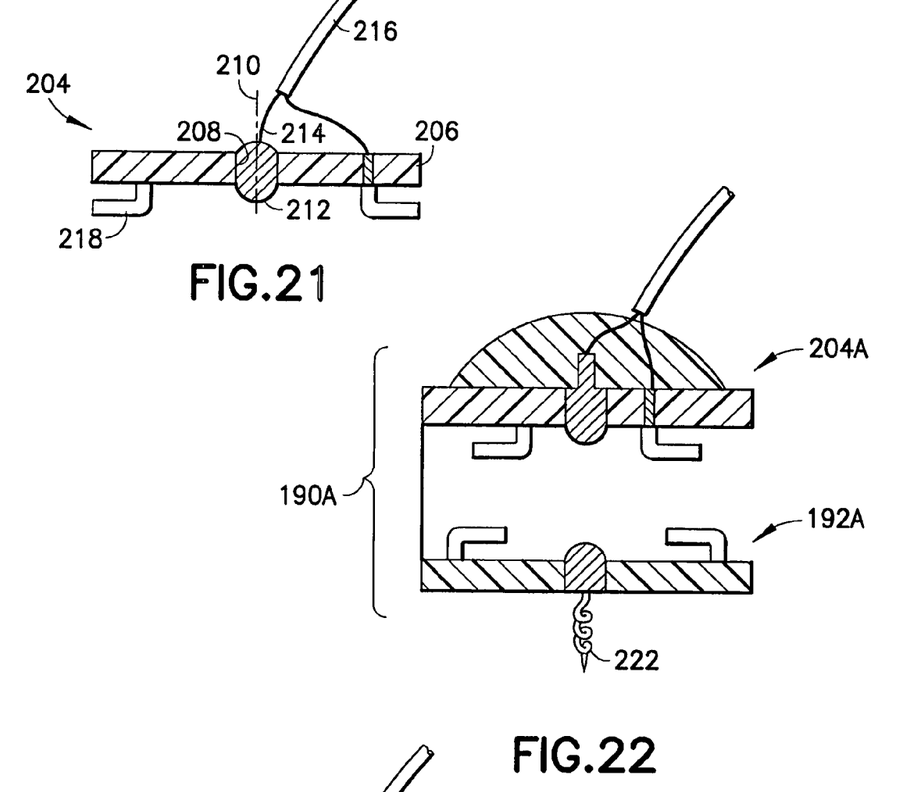
FIG. 21 is a detail elevation view, in cross section, of a part of the electrode head illustrated in FIG. 20.
FIG. 22 is a detail elevation view, in cross section, of still a further embodiment of an electrode head with an electrode tip member and an electrode backing member in their separated condition.

Turn now to FIGS. 20 and 21 which illustrate another embodiment of the lead assembly. In this instance, an electrode head 190 includes an electrode tip member 192 with a first disk-shaped non-conductive base 194 of polyurethane or other suitable material and a first central through bore 196 aligned with a first axis 198 perpendicular to the first non-conductive base. A tip electrode 200 is mounted on and projects away from the non-conductive base 194 in one direction and a plurality of first I-shaped tab members 202 fixed to the base 194 are equally spaced from the tip electrode 200 and project away from the base in an opposite direction at a plurality of circumferentially spaced locations.

An electrode backing member 204 includes a second disk-shaped non-conductive base 206 having a second central through bore 208 aligned with a second axis 210 perpendicular to the second non-conductive base 206. An electrical contact 212 mounted in the second central through bore 208 is electrically connected with a conductor 214 from a lead body 216.

A plurality of second L-shaped tab members 218 are equally spaced from the electrical contact 212 and project away from the second non-conductive base 206 toward the first non-conductive base 194 at a plurality of circumferentially spaced locations. With this arrangement, upon mutual alignment of the first and second axes 198, 210, respectively, and with movement of the second non-conductive base 206 toward the first non-conductive base 194, then rotation of the first non-conductive base relative to the second non-conductive base, the first and second tab members 202, 218 become engaged and the tip electrode 200 and electrical contact 212 become engaged thereby releasably but firmly integrating the electrode tip member 192 and the electrode backing member 204 as a unit (see FIGS. 20A and 20B).

As in the earlier described embodiments, a non-conductive cap member 220 is applied to proximally overlie the electrode backing member 204.

In the instance of the FIG. 20 embodiment, the tip electrode 200 is a passive fixation electrode, typically being held in place by use of suture material.

In another instance illustrated in FIG. 22, an electrode head 190A is modified such that a tip electrode 192A is an active fixation electrode utilizing a helical screw 222 in the usual fashion. For the electrode head 192A, an electrode backing member 204A remains unchanged from the FIG. 20 embodiment. As in previous embodiments, the electrode heads 190 and 190A (FIGS. 20 and 22) employ a unipolar tip electrode.

Figure 23:
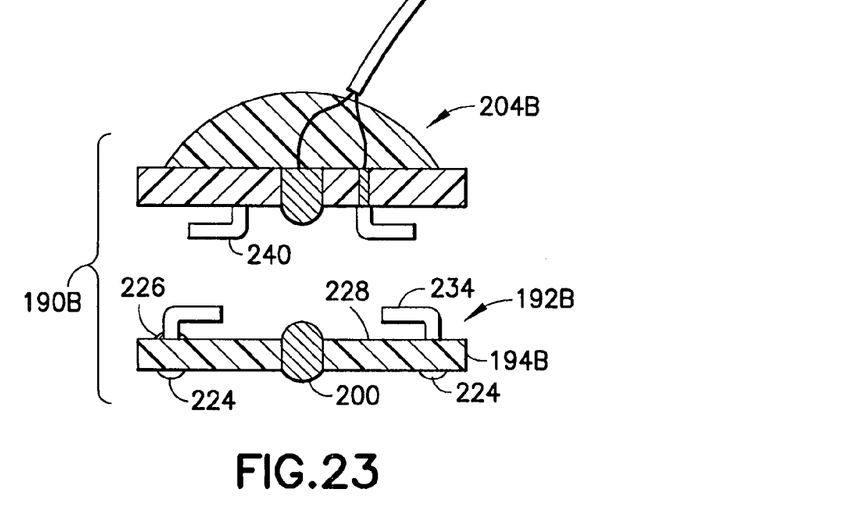
FIG. 23 is a detail elevation view, in cross section, of a further embodiment of an electrode head with an electrode tip member and an electrode backing member in their separated condition.
Figure 24:
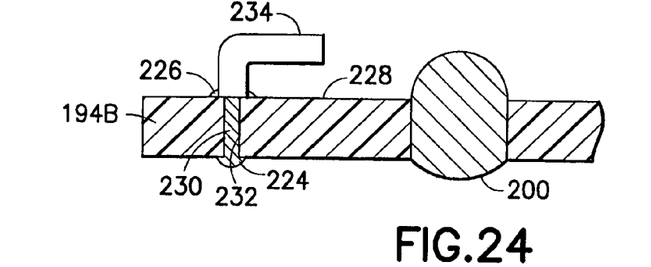
FIG. 24 is a detail cross section view of components illustrated in FIG. 23.
Figure 25:
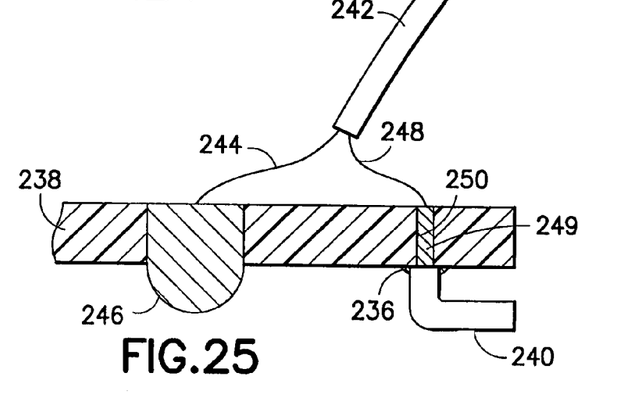
FIG. 25 is another detail cross section view of components illustrated in FIG. 23.

Turn now to FIGS. 23, 24, and 25 which present a generally similar construction to that of FIGS. 20–21 but one of a bipolar electrode configuration. In this instance, for an electrode head 190B incorporating an electrode tip member 192B and an electrode backing member 204B, a ring electrode 224 is mounted on and projects away from a first non-conductive base 194B in one direction, the ring electrode being spaced from the tip electrode 200. A first ring contact 226 is mounted on a first planar surface 228 and a connection branch 230 received in a bore 232 through the first non-conductive base 194B electrically connects the ring electrode 224 and the first ring contact 226. The first ring contact 226 electrically connects each of a plurality of first L-shaped tab members 234 having the nature of the tab members 202.

A second ring contact 236 is mounted on a second non-conductive base 238 electrically connecting each of a plurality of second L-shaped tab members 240 having the nature of the tab members 218. A lead body 242 having the nature of the lead body 216 includes a first conductor 244 attached to an electrical contact 246 in the second non-conductive base 238 for eventual connection with the tip electrode 200. The lead body 242 includes a second conductor 248 attached to a conductive branch 249 received in a bore 250 in the second non-conductive base 238 to the second ring contact 236 for connection with the ring electrode 224 when the electrode tip member 192B and the electrode backing member 204B are firmly integrated as a unit.

In the instance of the FIGS. 20 and 23 embodiments, the tip electrode 200 is a passive fixation electrode, typically being held in place by use of suture material.

Figure 26:
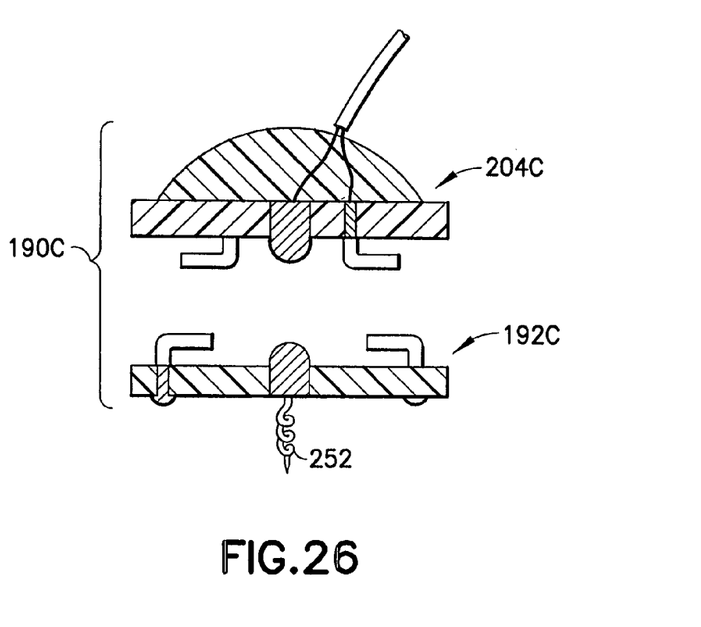
FIG. 26 is a detail elevation view, in cross section, of still another embodiment of an electrode head with an electrode tip member and an electrode backing member in their separated condition.

In yet another instance illustrated in FIG. 26, an electrode head 190C is modified such that a tip electrode 192C is an active fixation electrode utilizing a helical screw 252 in the usual fashion. For the electrode head 190C, an electrode backing member 204C remains unchanged from the FIG. 23 embodiment.

It should be understood that the foregoing description is only illustrative of the various embodiments disclosed. Various alternatives and modifications can be devised by those skilled in the art without departing from the spirit and scope of the invention. Accordingly, the present invention is intended to embrace all such alternatives, modifications and variances which fall within the scope of the appended claims.

What is claimed is:

1. An implantable, epicardial lead adapted to conduct electrical stimulation from an electrical stimulator to an epicardial site of the heart and to conduct electrical signals of the heart from the epicardial site to the electrical stimulator, the implantable epicardial lead comprising:

an elongated lead body defining a lead body distal end and a lead body proximal end, and comprising a connector at the lead body proximal end for mechanical and electrical attachment to the electrical stimulator, and further comprising a conductor extending between the lead body distal end and lead body proximal end; and an electrode head provided at the lead body distal end including an electrode tip member adapted to be fixated to the outside of the heart and an electrode backing member fixed to the distal end of the lead body and releasably attachable to the electrode tip member to establish electrical contact between the electrode tip member and the lead body, a planar surface at a distal end of the electrode tip member to establish contact with the outside of the heart;

a tip electrode disposed at the planar surface of the electrode tip member, the elongated lead body being coupled to the electrode head such that the lead body distal end is moveable from a first position wherein a longitudinal axis of the lead body distal end is substantially perpendicular to the planar surface to a second position wherein the longitudinal axis of the lead body distal end is substantially parallel to the planar surface when the tip electrode is in electrical contact with the outside of the heart;

wherein the electrode tip member comprises:
a first non-conductive and disc-shaped base;
the tip electrode mounted on and projecting away from the first base in one direction; and
the first base having a first mounting member directed away from the tip electrode; and wherein the electrode backing member comprises:
a second non-conductive and disc-shaped base; and
a second mounting member cooperatively received on the second base and adapted for mounting engagement with the first mounting member for releasably but firmly integrating the electrode tip member and the electrode backing member as a unit.

2. The implantable lead as set forth in claim 1:
wherein the first mounting member includes a centrally located tapped bore in the first base;
wherein the second base has a central smooth bore nearest the electrode tip member, an enlarged counterbore in communication with the central bore and extending farther away from the electrode tip member, and an annular shelf intermediate the central bore and the enlarged counterbore; and
wherein the second mounting member includes a screw member attached to the lead body and including a head, a threaded shank, and a shoulder intermediate the head and the threaded shank; and
wherein the threaded shank is slidably received through the central bore with the shoulder of the screw member engageably received on the annular shelf, the threaded shank being threadedly engaged with the tapped bore of the first base and rotated about its axis until firm integration of the electrode tip member and of the electrode backing member has occurred.

3. The implantable lead as set forth in claim 2:
wherein the first base has the planar surface facing the second base;
wherein the second base has an additional planar surface facing the planar surface, the planar surface and the additional planar surface being contiguously engaged when the electrode tip member and the electrode backing member are firmly integrated as a unit.

4. The implantable lead as set forth in claim 3 including:
a ring electrode mounted on and projecting away from the first base in one direction, the ring electrode disposed at the planar surface of the electrode tip member and being spaced from the tip electrode to form a bipolar electrode configuration;
a ring contact mounted on the planar surface;
a connection branch received in a bore through the first base electrically connecting the ring electrode and the ring contact;
wherein the lead body includes a first lead attached to the screw member for connection with the tip electrode; and
wherein the lead body includes a second lead attached through a bore in the second base to a second contact on the additional planar surface for connection with the ring contact when the electrode tip member and the electrode backing member are firmly integrated as a unit.

5. The implantable lead as set forth in claim 1, wherein the tip electrode is a passive fixation electrode.

6. The implantable lead as set forth in claim 1, wherein the tip electrode is an active fixation electrode.

7. The implantable lead as set forth in claim 1 including a non-conductive cap member proximally overlying the electrode backing member.

8. The implantable lead as set forth in claim 1:
wherein the first base has the planar surface;
wherein the first mounting member includes a post having a contoured peripheral outer surface upstanding from the planar surface and extending to an outwardly projecting annular rim;
wherein the second non-conductive base has an additional planar surface and a contoured central bore extending away from the additional planar surface and generally configured congruently to the upstanding post, having an intermediate annular ridge and terminating beyond the annular ridge at an annular valley region distant from the additional planar surface;
such that the upstanding post may be slidably but fittingly received through the central bore until the annular rim engages the annular ridge, momentarily enlarging the diameter of the annular ridge, then be contiguously received by the annular valley region and, simultaneously, the planar surface and the additional planar surface become contiguously engaged whereupon firm integration of the electrode tip member and of the electrode backing member occurs.

9. The implantable lead as set forth in claim 1:
wherein the first base has the planar surface;
wherein the first mounting member includes a post having an extreme end and an outer peripheral surface with a first annular groove positioned intermediate the extreme end and the planar surface; and
wherein an annular coil spring is fittingly received in the second annular groove;
wherein the second base has an additional planar surface and a central bore extending away from the additional planar surface and a second annular groove spaced from the additional planar surface; and
wherein an annular coil spring is fittingly received in the second annular groove;
such that the upstanding post may be slidably received through the central bore until the extreme end engages the coil spring and, with continued movement of the post relative to the coil spring, the first annular groove engageably receives the annular coil spring and, simultaneously, the planar surface and the additional planar surface become contiguously engaged whereupon firm integration of the electrode tip member and of the electrode backing member occurs.

10. An implantable, epicardial lead adapted to conduct electrical stimulation from an electrical stimulator to an epicardial site of the heart and to conduct electrical signals of the heart from the epicardial site to the electrical stimulator, the implantable epicardial lead comprising:
an elongated lead body defining a lead body distal end and a lead body proximal end, and comprising a connector at the lead body proximal end for mechanical and electrical attachment to the electrical stimulator, and further comprising a conductor extending between the lead body distal end and lead body proximal end; and
an electrode head provided at the lead body distal end including an electrode tip member adapted to be fixated to the outside of the heart and an electrode backing member fixed to the distal end of the lead body and releasably attachable to the electrode tip member to establish electrical contact between the electrode tip member and the lead body, a planar surface at a distal end of the electrode tip member to establish contact with the outside of the heart;
a tip electrode disposed at the planar surface of the electrode tip member, the elongated lead body being coupled to the electrode head such that the lead body distal end is moveable from a first position wherein a longitudinal axis of the lead body distal end is substantially perpendicular to the planar surface to a second position wherein the longitudinal axis of the lead body distal end is substantially parallel to the planar surface when the tip electrode is in electrical contact with the outside of the heart;
wherein the electrode tip member comprises:
a first non-conductive base;
the tip electrode mounted on and projecting away from the first non-conductive base in one direction; and
the first base having a first mounting member directed away from the tip electrode, a longitudinal axis of the first mounting member being parallel to a longitudinal axis of the tip electrode; and
wherein the electrode backing member comprises:
a second non-conductive base; and
a second mounting member cooperatively received on the second non-conductive base and adapted for mounting engagement with the first mounting member for releasably but firmly integrating the electrode tip member and the electrode backing member as a unit, a longitudinal axis of the second mounting member being parallel to the longitudinal axis of the first mounting member and the longitudinal axis of the tip electrode.

11. The implantable lead as set forth in claim 10:
wherein the first mounting member includes a centrally located tapped bore in the first non-conductive base;
wherein the second non-conductive base has a central smooth bore nearest the electrode tip member, an enlarged counterbore in communication with the central bore and extending farther away from the electrode tip member, and an annular shelf intermediate the central bore and the enlarged counterbore; and
wherein the second mounting member includes a screw member attached to the lead body and including a head, a threaded shank, and a shoulder intermediate the head and the threaded shank; and
wherein the threaded shank is slidably received through the central bore with the shoulder of the screw member engageably received on the annular shelf, the threaded shank being threadedly engaged with the tapped bore of the first non-conductive base and rotated about its axis until firm integration of the electrode tip member and of the electrode backing member has occurred.

12. The implantable lead as set forth in claim 11:
wherein the first non-conductive base has the planar surface facing the second non-conductive base;
wherein the second non-conductive base has an additional planar surface facing the planar surface, the planar surface and the additional planar surface being contiguously engaged when the electrode tip member and the electrode backing member are firmly integrated as a unit.

13. The implantable lead as set forth in claim 12 including:
a ring electrode mounted on and projecting away from the first non-conductive base in one direction, the ring electrode disposed at the planar surface of the electrode tip member and being spaced from the tip electrode to form a bipolar electrode configuration;
a ring contact mounted on the planar surface;
a connection branch received in a bore through the first base electrically connecting the ring electrode and the ring contact;
wherein the lead body includes a first lead attached to the screw member for connection with the tip electrode; and
wherein the lead body includes a second lead attached through a bore in the second non-conductive base to a second contact on the additional planar surface for connection with the ring contact when the electrode tip member and the electrode backing member are firmly integrated as a unit.

14. The implantable lead as set forth in claim 10, wherein the tip electrode is a passive fixation electrode.

15. The implantable lead as set forth in claim 10, wherein the tip electrode is an active fixation electrode.

16. The implantable lead as set forth in claim 10:
wherein the first base has the planar surface;
wherein the first mounting member includes a post having a contoured peripheral outer surface upstanding from the planar surface and extending to an outwardly projecting annular rim;

wherein the second non-conductive base has an additional planar surface and a contoured central bore extending away from the additional planar surface and generally configured congruently to the upstanding post, having an intermediate annular ridge and terminating beyond the annular ridge at an annular valley region distant from the additional planar surface;

such that the upstanding post may be slidably but fittingly received through the central bore until the annular rim engages the annular ridge, momentarily enlarging the diameter of the annular ridge, then be contiguously received by the annular valley region and, simultaneously, the planar surface and the additional planar surface become contiguously engaged whereupon firm integration of the electrode tip member and of the electrode backing member occurs.

* * * * *